United States Patent
Smith (10) Patent No.: US 10,905,370 B2
(45) Date of Patent: Feb. 2, 2021

(54) ALLERGY SKIN TEST DEVICES

(71) Applicant: Rememdia LC, Salt Lake City, UT (US)

(72) Inventor: Fraser M. Smith, Salt Lake City, UT (US)

(73) Assignee: Rememdia LC, Salt Lake City, UT (US)

( * ) Notice: Subject to any disclaimer, the term of this patent is extended or adjusted under 35 U.S.C. 154(b) by 319 days.

(21) Appl. No.: 15/920,405

(22) Filed: Mar. 13, 2018

(65) Prior Publication Data

US 2018/0199878 A1 Jul. 19, 2018

Related U.S. Application Data

(62) Division of application No. 14/796,783, filed on Jul. 10, 2015, now abandoned.

(51) Int. Cl.
| | | |
|---|---|---|
| *A61B 5/04* | (2006.01) | |
| *A61B 5/00* | (2006.01) | |
| *A61B 5/103* | (2006.01) | |
| *A61B 5/01* | (2006.01) | |

(52) U.S. Cl.
CPC ............ *A61B 5/411* (2013.01); *A61B 5/0077* (2013.01); *A61B 5/1032* (2013.01); *A61B 5/7282* (2013.01); *A61B 5/015* (2013.01); *A61B 5/6898* (2013.01); *A61B 5/742* (2013.01); *A61B 5/7405* (2013.01); *A61B 5/7455* (2013.01); *A61B 2562/0276* (2013.01); *A61B 2562/08* (2013.01)

(58) Field of Classification Search
CPC ........ A61B 2562/0276; A61B 2562/08; A61B 5/0077; A61B 5/015; A61B 5/1032; A61B 5/411; A61B 5/6832; A61B 5/6898; A61B 5/7282; A61B 5/7405; A61B 5/742; A61B 5/7455

See application file for complete search history.

(56) References Cited

U.S. PATENT DOCUMENTS

| | | |
|---|---|---|
| 4,214,592 A | 7/1980 | Jacquet et al. |
| 4,473,083 A | 9/1984 | Maganias |
| 4,480,638 A | 11/1984 | Schmid |
| 4,802,493 A | 2/1989 | Maganias |

(Continued)

OTHER PUBLICATIONS achooallergy.com, https://www.achooallergy.com/my-allergy-test/, to the best of applicant's knowledge article was available before the application filing date, 6 pages.

(Continued)

*Primary Examiner* — Mark D Remaly (57) ABSTRACT

An allergy skin test device can include a support strip having a top and bottom face. An allergen can be applied to an area of the bottom face forming an allergen portion. A skin viewing portion can be located proximate or at the allergen portion. An adhesive can be applied to an area of the bottom face forming an adhesion portion. When applied to the skin of a subject, the allergy skin test device can facilitate viewing of a portion of the skin beneath the allergy skin test device through the skin viewing portion. A method of testing a subject for an allergy can include applying an allergy skin test device to the skin of the subject, recording two or more images of the skin of the subject, and electronically comparing the images.

22 Claims, 6 Drawing Sheets

(56) References Cited

U.S. PATENT DOCUMENTS

| | | | |
|---|---|---|---|
| 4,836,217 A | 6/1989 | Fischer | |
| 4,887,611 A | 12/1989 | Rudiger et al. | |
| 5,104,620 A | 4/1992 | Wiley et al. | |
| 5,182,081 A | 1/1993 | Hedegaard et al. | |
| 5,614,167 A | 3/1997 | Hansen et al. | |
| 7,635,488 B2 | 12/2009 | Dupont et al. | |
| 7,722,897 B2 | 5/2010 | Dupont et al. | |
| 7,896,816 B2 | 3/2011 | Utsugi | |
| 7,942,827 B2 | 5/2011 | Mir et al. | |
| 8,723,986 B1 * | 5/2014 | Merrill, Jr. | H04N 5/232 348/207.99 |
| 8,734,697 B2 | 5/2014 | Chen et al. | |
| 2004/0044294 A1 | 3/2004 | Utsugi | |
| 2007/0014728 A1 | 1/2007 | Imbert et al. | |
| 2014/0358082 A1 * | 12/2014 | Ohzawa | A61B 5/4839 604/151 |
| 2016/0367152 A1 | 12/2016 | Stepien | |

OTHER PUBLICATIONS

Dailymed, T.R.U.E. Test Thin-Layer Rapid Use Patch Test, https://dailymed.nlm.nih.gov/dailymed/drugInfo.cfm?setid=2f082b68-dc74-418a-9e6f-b3c285b41d44&CFID=424236&CFTOKEN=1a337e74f789fada-953EF561-A52C-760C-03857EE2B678108B, Nov. 7, 2014, 4 pages, National Library of Medicine.

Immunetech, Inc., https://www.myallergytest.net/howitworks.php. to the best of applicant's knowledge article was available before the application filing date, 1 page, Foster City, CA.

Mayo Clinic, Allergy skin tests, http://www.mayoclinic.org/tests-procedures/allergy-tests/basics/what-you-can-expect/prc-20014505, Apr. 2, 2014, 3 pages, Mayo Foundation for Medical Education and Research.

Sweetwater Health, Find Your Kryptonite With the Free Bulletproof Food Sense iPhone App!, to the best of applicant's knowledge article was available before the application filing date, 5 page.

* cited by examiner

ALLERGY SKIN TEST DEVICES

RELATED APPLICATIONS

This is a divisional application of U.S. application Ser. No. 14/796,783, filed Jul. 10, 2015, entitled "Allergy Skin Test Devices" which is incorporated by reference in its entirety herein.

BACKGROUND

Millions of people suffer from allergies to various substances. An allergy is a hypersensitivity disorder, in which the immune system over-responds to a substance in the environment. The seriousness of allergic reactions can range from slight to severe. Many less serious allergic reactions cause runny nose, itching, internal discomfort and so on. Severe allergic reactions can cause bronchoconstriction, edema, hypotension, coma, and even death. Many different substances can potentially trigger allergic reactions. Common allergens include pollen, animal dander, foods, pharmaceuticals, latex, and metals.

Allergy testing has been used to determine whether an individual is allergic to a particular substance. An individual may seek allergy testing if the individual is experiencing allergy symptoms, but does not know which allergen is causing the symptoms. Alternatively, an individual may wish to know of an allergy ahead of time so that the individual will know which allergens to avoid. A variety of methods for diagnosing allergies have been developed. Skin prick tests involve placing an allergen on the skin and then pricking the skin so that the allergen contacts cells beneath the skin's surface. A health care provider can observe the pricked area and diagnose an allergy based on swelling, redness, or other signs of reaction. Intradermal skin tests involve injecting allergen under the skin. A health care provider can then observe the injection site for allergic reactions. Allergies can also be diagnosed using blood tests. A blood sample can be drawn and then tested for the presence of certain antibodies that indicate an immune response to a particular allergen.

BRIEF DESCRIPTION OF THE DRAWINGS

Features and advantages of the invention will be apparent from the detailed description which follows, taken in conjunction with the accompanying drawings, which together illustrate, by way of example, features of the invention; and, wherein.

Reference will now be made to the exemplary embodiments illustrated, and specific language will be used herein to describe the same. It will nevertheless be understood that no limitation of the scope of the invention is thereby intended.

DETAILED DESCRIPTION

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

An initial overview of technology embodiments is provided below and then specific technology embodiments are described in further detail later. This initial summary is intended to aid readers in understanding the technology more quickly but is not intended to identify key features or essential features of the technology nor is it intended to limit the scope of the claimed subject matter.

The present disclosure is directed towards allergy skin test devices and methods for testing a subject for an allergy. More specifically, the present disclosure relates to devices and methods that can be easily purchased over the counter and which are sufficiently reliable and easy to use so that an individual can perform the allergy test at home without supervision of a health care professional.

Previous solutions for allergy testing have generally required a doctor or other health care professional to obtain, read and interpret test results. For example, in skin prick tests, a health care professional administers the allergen and skin prick at the beginning of the test, and then observes the skin and interprets any skin reaction that develops. Therefore, the individual undergoing the test relies on the health care professional to determine if the individual has an allergy. In many cases, such an allergy test requires a long wait up to several hours at the health care professional's office to read the test results. In other cases, a waiting period of multiple days is required between administering the allergen and reading the results. This necessitates multiple trips to see the health care professional. If an allergy test is negative, it is often necessary to begin another test for a different allergen and make additional trips to see the health care professional. Thus, allergy tests administered by health-care professionals can require significant inconveniences and time commitments for the individual undergoing the tests. Visits to health care professionals can also be a financial burden. This results in loss of time and money for individuals receiving allergy tests and can also prompt some individuals to continue suffering allergy symptoms rather than undergo testing to identify the individuals' allergies.

The allergy testing devices and methods according to the present disclosure can reduce the time and financial cost of receiving allergy testing. The testing devices can be used at home by any individual with minimal or no at home training. The tests can have high accuracy and high sensitivity. Testing methods can include using computerized systems, such as smartphones, which have advantages of being able to detect small differences in skin color that even a trained healthcare professional would not see. These computerized systems also allow for comparing an individual's allergic reaction with data from many other individuals, so that the type and severity of the individual's allergy can be most accurately identified. These and other advantages of the present technology are described in more detail below.

In one aspect, the present technology relates to an allergy skin test device. An allergy skin test device can include a support strip having a top face and a bottom face. An allergen can be applied to or about an area of the bottom face forming an allergen portion. A skin viewing portion can be located proximate or at the allergen portion. Additionally, an adhesive can be applied to an area of the bottom face forming an adhesion portion. When applied to the skin of a subject, the allergy test device can facilitate viewing of a portion of the skin beneath the allergy test device through the skin viewing portion, such as for the purpose of viewing an allergic reaction while the support strip is maintained on the skin.

Figure 1:
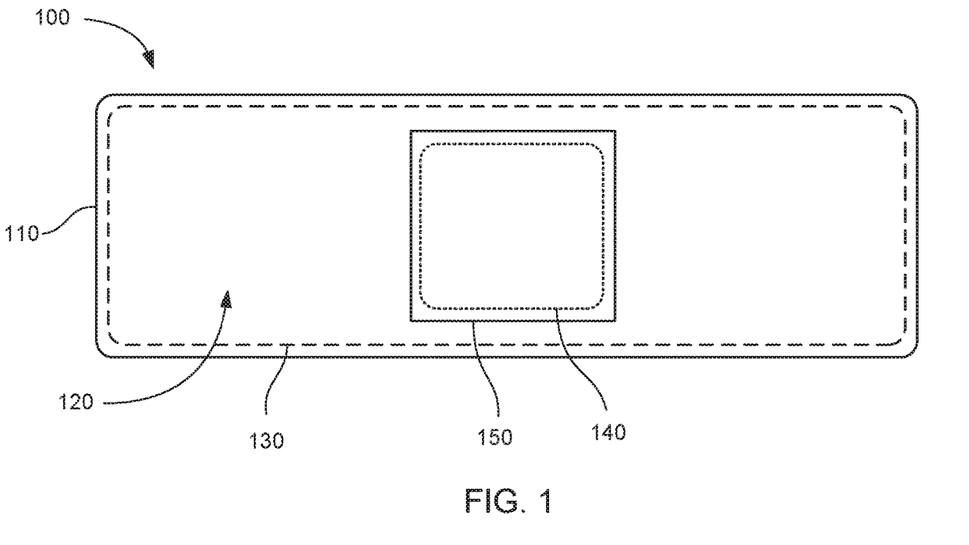
FIG. 1 is a top view of an allergy skin test device in accordance with an embodiment of the present invention.
Figure 2:
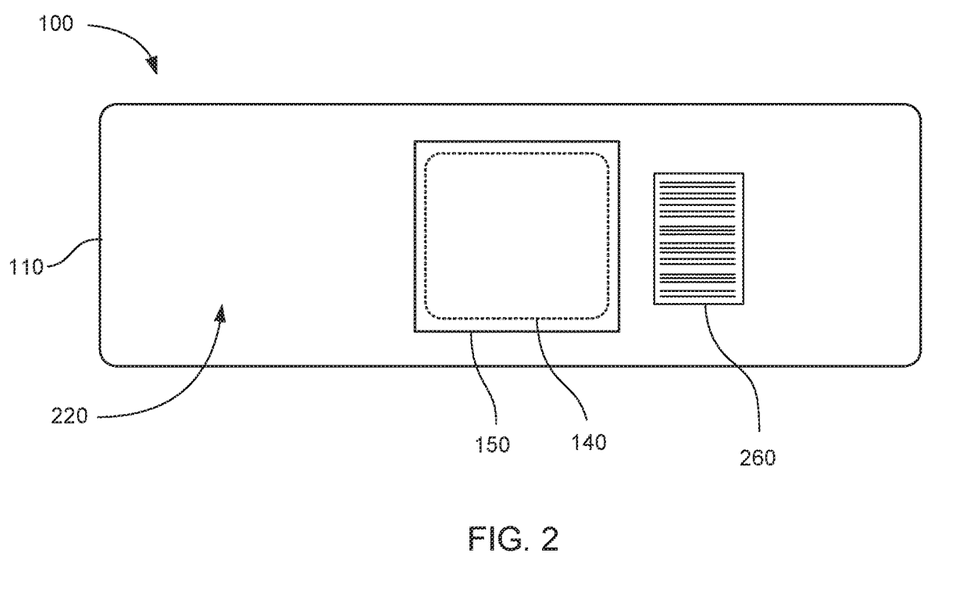
FIG. 2 is a bottom view of the allergy skin test device shown in FIG. 1.

A specific embodiment of an allergy skin test device is shown in FIGS. 1 and 2. FIG. 1 shows the allergy skin test device 100 as viewed from the bottom. The allergy skin test device includes a support strip 110 having a bottom face 120. An adhesive area 130 is denoted by a large dashed line. Adhesive is applied to the bottom space inside this area. An allergen portion 140 is denoted by a small dotted line. An allergen is applied to, or otherwise caused to be located at, the area in the allergen portion. A skin viewing portion 150 is located in a central area of the support strip, encompassing the allergen portion. In the specific embodiment shown, the skin viewing portion is a transparent window in the support strip that allows the entire allergen portion to be visible through the support strip. In some embodiments, the adhesive can cover the allergen portion. In other embodiments, the adhesive portion can end at the border of the allergen portion or at the border of the skin viewing portion. This can prevent false positives in subjects that have an allergy to the adhesive.

FIG. 2 shows the same allergy skin test device as shown in FIG. 1 viewed from the top. The allergy skin test device 100 includes a support strip 110 having a top face 220. The skin viewing portion 150 can comprise a window that allows viewing of the allergen portion 140 through the support strip. An identification code 260 is printed on the top surface of the support strip near the skin viewing portion. In the specific embodiment shown, the identification code is a bar code that can be read by an imaging device.

In some embodiments, the skin viewing portion can include a transparent portion formed within the support strip. For example, the allergen portion can be transparent with a transparent allergen. If the allergen is opaque, then there can be a transparent window adjacent to the allergen portion. For example, a small transparent window can be at the center of the allergen portion, with no allergen present beneath the window. Alternatively, the viewing portion can be on a side of the allergen portion, or can surround the allergen portion. Alternatively, the entire support strip can be transparent.

The transparent portion can be formed from a transparent material such as a transparent polymer. Examples of transparent polymers can include polypropylene (PP), polyethylene (PE), polyethylene terephthalate (PET), polycarbonate (PC), polyvinyl chloride (PVC), polyvinylidene chloride (PVDC), poly(methyl methacrylate) (PMMA), polystyrene (PS), styrene acrylonitrile (SAN), combinations thereof, and others transparent polymers.

In further embodiments, the skin viewing portion can include an aperture through the support strip. For example, the aperture can be a hole or slit penetrating through the support strip. In one example, the aperture can be oriented in a central area of the allergen portion. When the device is applied to the skin of a subject, the device can facilitate viewing of an exposed area of the skin through the aperture. The aperture can have a diameter of about 1 mm to about 1 cm, although this should not be considered limiting in any way.

Figure 3:
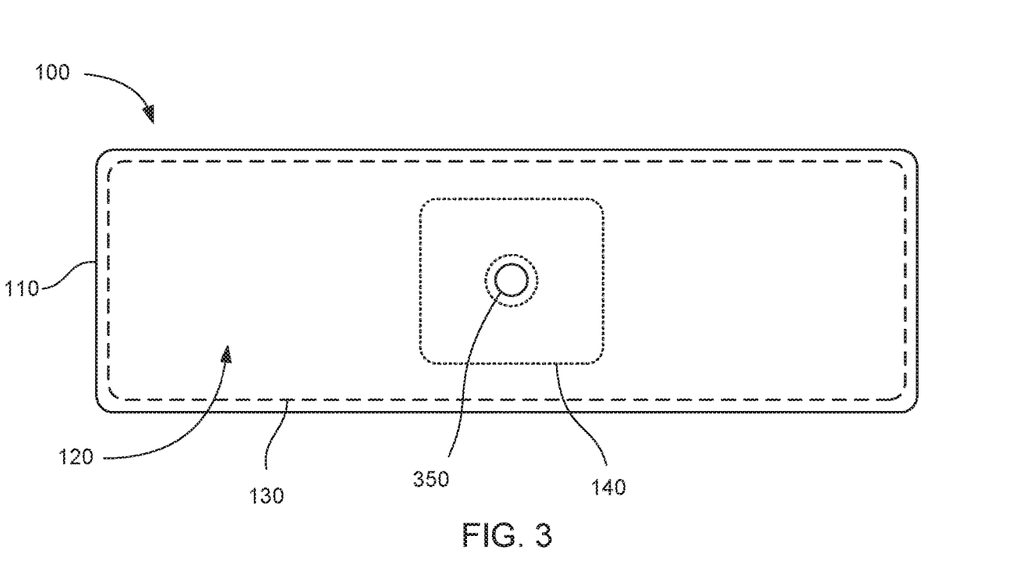
FIG. 3 is a top view of an allergy skin test device in accordance with an embodiment of the present invention.
Figure 4:
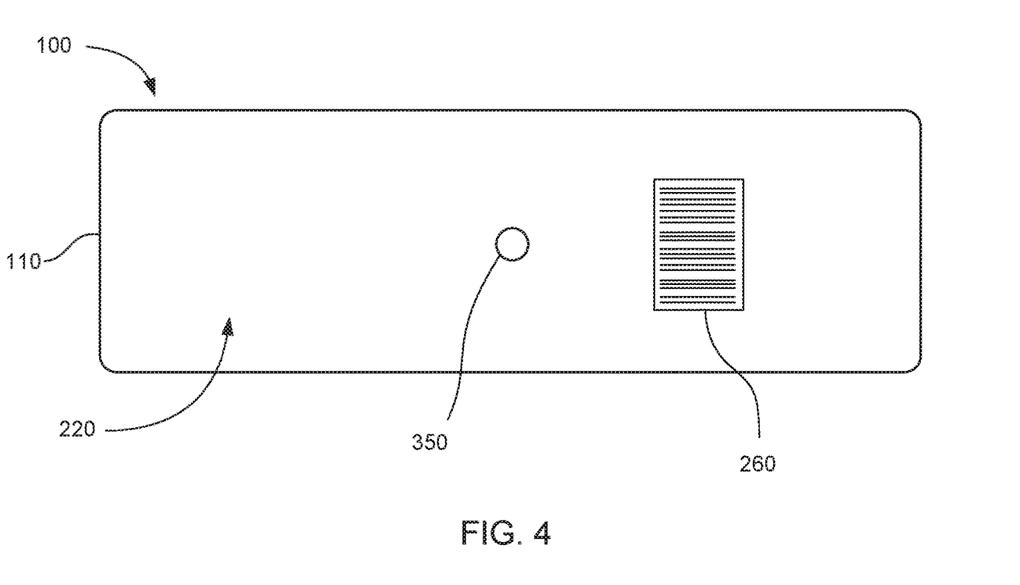
FIG. 4 is a bottom view of the allergy skin test device shown in FIG. 3.

FIGS. 3 and 4 show an allergy skin test device 100 having an aperture 350 through the support strip 110. FIG. 3 shows the device as viewed from the bottom, with an adhesive portion 130 and allergen portion 140 on the bottom face 120. In the specific embodiment shows, the adhesive portion 130 surrounds the aperture 350. This arrangement can expose the skin of the subject to the allergen in areas surround the aperture 350, so that if an allergic reaction occurs the reaction will be visible through the aperture 350. The allergen portion 140 is shown as having a circular border slightly outside the border of the aperture 350. However, in other embodiments, the allergen portion can extend all the way to the border of the aperture. FIG. 4 shows the same allergy skin test device 100 as viewed from above. The aperture 350 allows viewing of the skin of the subject through the aperture 350. An identification code 260 is printed on the top face 220 of the support strip 110.

Some allergies can be effectively tested by external skin contact only. However, other allergies can be more effectively tested if the allergen is delivered beneath the outermost layer of skin. Some allergens can be delivered into the epidermis, while others can be delivered beneath the epidermis. Accordingly, in some embodiments the allergy skin test device can comprise or further comprise features for piercing the outermost layer of skin to deliver allergen into the skin. In one embodiment, the allergy skin test device can include micro spicules located about the allergen portion. Micro spicules, also referred to as "micro needles," can be very small, sharp spikes located on or around the allergen portion. Generally, the micro spicules can be placed in a location on the test device where a skin puncture from the micro spicules can allow allergen to pass below the outer layer of skin. The micro spicules can be operable to pierce the skin of the subject when the allergy skin test device is applied to the skin. Thus, the allergen can penetrate a lower layer of the skin of the subject.

In some examples, the micro spicules can be formed from a hypoallergenic material so as to avoid causing allergic reactions due to the micro spicules themselves. The micro spicules can be formed from surgical steel, silicon, a hypoallergenic polymer, or combinations thereof. In one approach, the micro spicules can be formed of a biodegradable material. Biodegradable micro spicules can effectively create the small skin punctures necessary to deliver allergen beneath the outer layer of skin, and then the micro spicules can dissolve or otherwise degrade over a period of time. In one example, the micro spicules can be formed from sugar. Sugar micro spicules can pierce the skin and then dissolve and be metabolized in the body. In a further example, a mixture of sugar with the allergen can be used to form the micro spicules, so that the allergen is delivered into the skin from the micro spicules (the micro spicules forming the allergen portion) as the micro spicules dissolve. Other non-limiting examples of biodegradable materials include biodegradable polymers such as polylactic acid, polyglycolic acid, and copolymers thereof.

The size of the micro spicules can vary depending on the desired penetration depth. In some embodiments, the micro spicules can be from about 1 micron to about 100 microns in length. Longer micro spicules can generally provide a deeper penetration and higher likelihood of allergic reaction, but also can cause more pain or discomfort when the allergy skin test device is applied. When sufficiently small micro spicules are used, the allergy skin test device can be applied with little or no pain while still maintaining efficacy.

Figure 5:
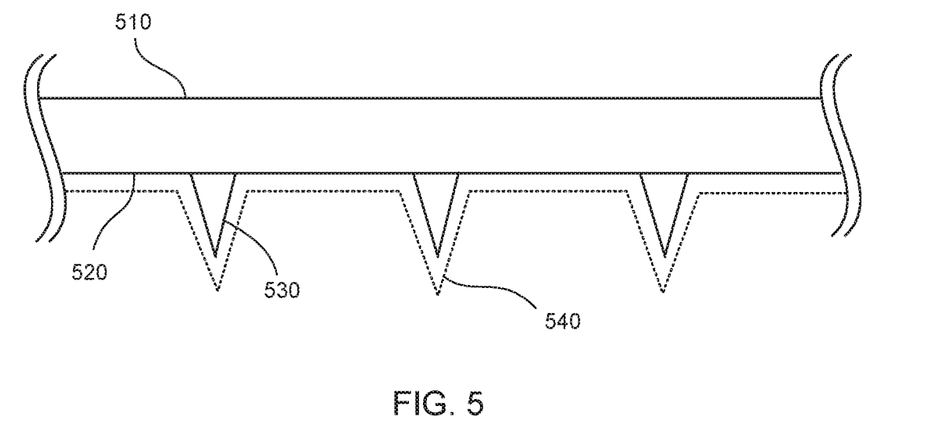
FIG. 5 is a side view of a portion of an allergy skin test device having micro spicules, in accordance with an embodiment of the present invention.

FIG. 5 shows a close up side view of a support strip section 510 of an allergy test device in accordance with another embodiment. The support strip section has a bottom face 520 with micro spicules 530 pointing downward. An allergen 540 is applied over the micro spicules. When the support strip is applied to the skin of a subject, the micro spicules can pierce the outer layer of skin and deliver the allergen beneath the outer layer of skin. In various embodiments, the micro spicules can be formed as an integral part of the support strip or they can be separate components attached to the support strip.

In some cases, multiple allergy skin test devices can be manufactured to test for a single allergen at different strength levels. For example, a low strength test device can have a low concentration of an allergen, while a high strength test device can have a high concentration of allergen. A subject having a very high sensitivity to the allergen may react to the lowest strength level of test device, while a subject with a moderate sensitivity may only react to a high strength level. In addition to using a higher concentration of allergen in higher strength test devices, micro spicules can be included to pierce the skin of the subject. The micro spicules can generally increase the likelihood that a subject will react to an allergen. Therefore, a subject with a low sensitivity to an allergen may show a skin reaction to an allergy test device including micro spicules.

The allergy skin test device can include an identification code printed on the top face of the support strip. The identification code can contain information about the allergy test device, such as the type of allergen, strength level of the test device, dose of allergen, presence or lack of micro spicules, expiration date, and so on. In some cases, the identification code can be a machine-readable code such as a bar code or QR (quick response) code. In other cases, the identification code can be human-readable. For example, the code can include words and numbers such as the name of the allergen, strength level of the test device, dose of allergen, presence or lack of micro spicules, expiration date, and so on.

The allergy skin test device can include a single allergen applied to an area of the bottom face of the support strip, forming a single allergen portion on the support strip. Such allergy skin test devices can be convenient and easy to use, because a user can select any desired single allergen to test for allergic reactions. Thus, if a user is only interested in testing for a single allergy, the user only needs to apply the specific allergen being tested to the user's skin. Additionally, having a single allergen on a test device makes it easy to identify what allergen is being tested. There is no likelihood of confusing allergens as there may be with multiple allergens present on a single test device. If a user wishes to test for multiple allergens, then multiple test devices with different allergens can be applied. For example, a user can apply several allergy skin test devices along the user's arm or other area of skin.

In an alternative embodiment, the allergy skin test device can include multiple allergens applied to an area of the bottom face of the support strip. In one example, the test device can include a panel of similar allergens or allergens from a single class of allergens. Such a test device can allow for quickly testing a broad range of allergens and may be used to rule out a large number of allergens with a single test.

The allergen portion can include any type of allergen that a user may wish to test. Non-limiting examples of classes allergens that can be tested include animal products, plant pollens, spores, food products, pharmaceuticals, metals, chemicals, and others. Non-limiting specific allergens that can be tested include grass pollen, dust, dust mites, mold, cat and dog dander, latex, perfume, peanuts, tree nuts, shellfish, eggs, milk, meat, fruit, soy, wheat, gluten, aspirin, non-steroidal anti-inflammatories, antibiotics, anesthetics, bee sting venom, nickel, copper, chromium, and others.

The allergen can be in any convenient form in the allergen portion of the test device. Non-limiting examples include allergen in the form of a powder, a paste, a suspension, a liquid, a film, an allergen-impregnated pad, a solid monolithic form, and combinations thereof. Different allergens can lend themselves to being used in different forms in the allergy skin test devices. For example, small particulate allergens such as pollen and pet dander can be applied to the allergy skin test device in their natural particulate form, as a suspension in water or other solvent, as a suspension in a gel, as a mixture with a polymer, as a mixture with an adhesive, and so on. Food allergens can be dried if necessary and ground into powder, then applied in any of the above mentioned forms. Alternatively, in some cases a food allergy is caused by a specific substance in the food. This substance can be extracted from the food and used in the allergy skin test device in any of the above mentioned forms. Proteins from peanuts are one specific example of an allergen that can be extracted from a food. Chemical allergens can be mixed with a matrix to hold the allergen on the test device. The matrix can be formulated to release a sufficient amount of the allergen onto the skin to cause an allergic reaction if the user is allergic to the allergen in question. For example, a chemical allergen can be dissolved in water or other solvent, impregnated into a pad, mixed with a polymer, mixed with an adhesive, or otherwise formulated to be applied to the test device. Metal allergens like nickel and copper can be ground into powder form and applied in any of the above forms. Alternately, a solid metal plate or foil can be attached to the test device so that the metal plate comes into contact with the user's skin. In one embodiment, the metal plate can be formed with a hole at the skin viewing portion of the test device so that the skin can be visible through the hole.

In any of the above forms of allergen, the allergen portion of the allergy skin test device can be formulated so that the allergen can be quickly removed from the skin in case of a severe allergic reaction. Specifically, the allergen portion can be formulated so that little or no residual allergen remains on the skin, such as in the form of loose allergen powder or adhered adhesive film containing allergen, after the test device is removed.

Figure 6:
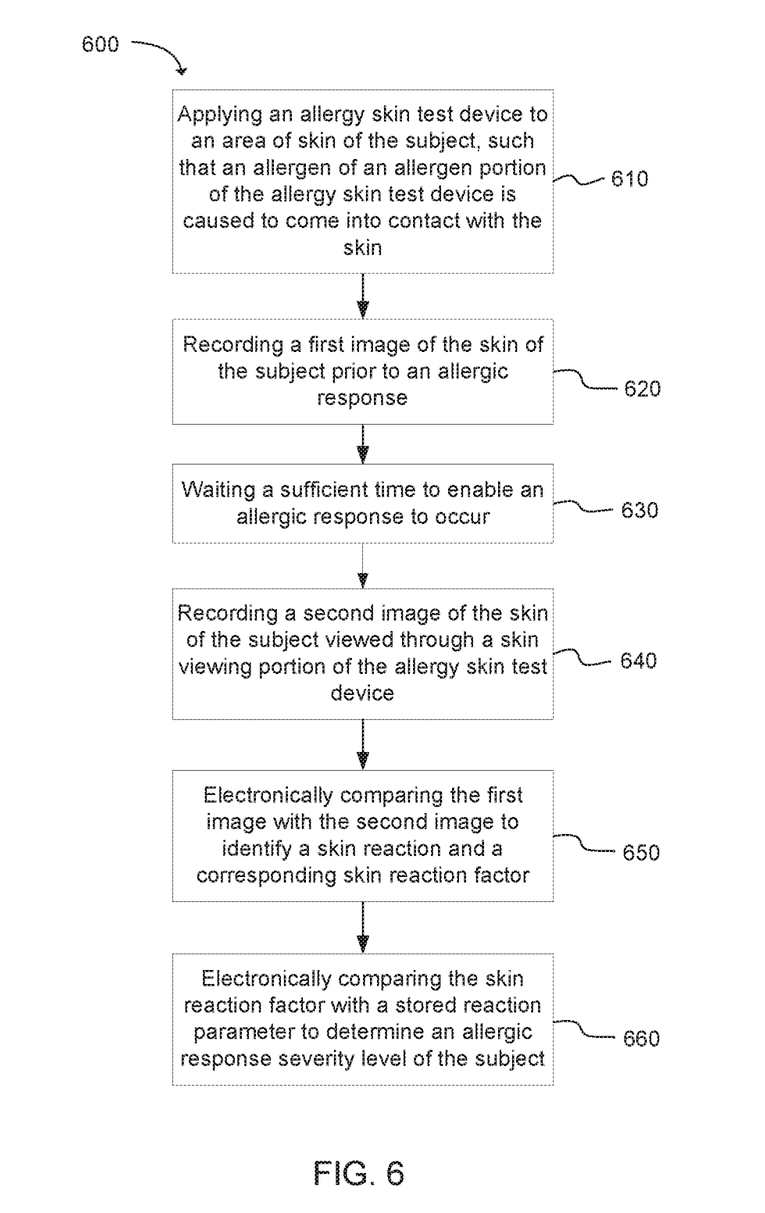
FIG. 6 is a flowchart illustrating a method of testing a subject for an allergy, in accordance with an embodiment of the present invention.

The present technology also extends to methods of testing a subject for an allergy. FIG. 6 shows a method of testing a subject for an allergy 600. The method includes, first, applying an allergy skin test device to an area of skin of the subject, such that an allergen of an allergen portion of the allergy skin test device is caused to come into contact with the skin 610. A first image is recorded of the skin of the subject prior to an allergic response 620. Next, the method includes waiting a sufficient time to enable an allergic response to occur 630. A second image of the skin of the subject viewed trough a skin viewing portion of the allergy skin test device is then recorded 640. The first image is electronically compared with the second image to identify a skin reaction and a corresponding skin reaction factor 650. Finally, the skin reaction factor is electronically compared with a stored reaction parameter to determine an allergic response severity level of the subject 660.

The allergy skin test device used in the method can have any of the features and characteristics described above. In some embodiments, the allergy skin test device can include a support strip having a top and bottom face. An allergen can be applied to an area of the bottom face forming an allergen portion. A skin viewing portion can be located proximate or at the allergen portion. An adhesive can be applied to an area of the bottom face forming an adhesion portion. The allergy skin test device can facilitate viewing of a portion of the skin beneath the allergy skin test device through the skin viewing portion.

In some embodiments, the allergy skin test device can include an identification code printed on the top face of the support strip. The identification code can identify a characteristic of the allergen. In some cases, the identification code can be machine-readable, such as a bar code or QR code. The identification code can be read electronically to provide information about the allergy skin test device. This information can be used in the method to help identify an appropriate stored reaction parameter to determine an allergic response severity level of the subject. In other cases, the identification code can be human-readable. However, a human-readable identification code can also be read electronically using an optical reading process such as optical character recognition (OCR).

In various embodiments, the steps of electronically comparing the first and second images and electronically comparing the skin reaction factor with the stored reaction parameter can be performed using a computer system comprising one or more processors. Non-limiting examples of computer systems include a personal computer (PC), a laptop, a smartphone, a tablet computer, a server and client system, and combinations thereof. In some embodiments, the method steps can be performed by a single computer or mobile device. In other embodiments, the method steps can be distributed between multiple computers, mobile devices, servers, clients, and so on. For example, in one embodiment, comparing the first and second images can be performed by a processor of a mobile device such as a smart phone. The stored reaction parameter can be stored in memory of the same mobile device, and the processor the mobile device can also be used to compare the skin reaction factor with the stored reaction parameter to determine an allergic response severity level. In another embodiment, a processor of the mobile device can be used to compare the first and second image and to compare the skin reaction factor with the stored reaction parameter, but the stored reaction parameter can be stored in memory of a server. In yet another embodiment, comparing the first and second images, storing the stored reaction parameter, and comparing the skin reaction factor with the stored reaction parameter can all be performed by a server, and a PC or mobile device can be used as a client for a user to access the server.

In some cases, the computer system can include a digital imaging device in communication with one or more processors of the computer system. In one example, the computer system can comprise a mobile device such as a smartphone or tablet with an integrated digital camera. Such a digital imaging device can be used to record the first and second images of the skin of the subject. In one example, the digital imaging device can also be used to read the identification code printed on the allergy skin test device. The identification code can be printed near the skin viewing portion so that the first and second images of the skin of the subject can include both the skin viewing portion of the allergy skin test device and the identification code. In one embodiment, the first and second images can be recorded using an integrated camera of a mobile device.

In some embodiments, the first image of the skin can be recorded as viewed through the skin viewing portion of the allergy skin test device. In other embodiments, the first image of the skin can be recorded before the allergy skin test device is applied. Therefore, the first image can be of bare skin. However, for the purpose of comparing the first and second images, it can be useful to record both images through the skin viewing portion of the allergy skin test device to make the images as similar as possible. Recording both images through the viewing portion of the allergy skin test device can enhance control parameters to ensure that the same area of skin is viewed in each image, and the major difference between the first image and the second image can be any change in appearance of the skin.

To further control the first and second images, a consistent light source can be used to illuminate the skin in each image. In some examples, the light source can be in communication with one or more processors of the computer system. In a specific example, the light source can be an integrated light of a mobile device. The integrated light can provide calibrated illumination to the skin. In one embodiment, the brightness of the integrated light can be adjusted to provide consistent illumination to the skin. The brightness of the light can be changed to compensate for other variables, such as the distance at which the user holds the mobile device from the skin when taking the images. Although a user may take the first and second images from different distances, the brightness of the integrated light of the mobile device can be adjusted so that a consistent amount of light reaches the skin. In one example, the mobile device can adjust the brightness of the light to an appropriate level by matching a reference point in the first and second images. One or more colors present on the top surface of the allergy skin test device can provide reference points for the mobile device to adjust the brightness. The brightness of the light used when recording the second image can be adjusted until the colors on the allergy skin test device match the colors as recorded in the first image. Thus, any change in skin color can be attributed to a skin reaction, and not to a difference in light brightness.

In further examples, the light source can be configured to emit a wavelength of light selected to improve detectability of the skin reaction. In many cases, a skin reaction can include an increase in redness of the skin. In these cases, the light source can be configured to emit green and blue light. Before an allergic reaction occurs, the skin can reflect green and blue light, but as the skin becomes redder, more green and blue light is absorbed. Therefore, images of the skin before and after the allergic reaction can have a high brightness contrast because the green and blue light is more strongly absorbed in the second image. The desired wavelengths of light can be produced, for example, by placing a filter in front of the light source. For example, a filter that filters out red light can be used in order to emit green and blue light. A filter can also be used to filter light entering an imaging device to make increased redness of the skin more apparent. In one example, a polymer film blue filter can be adhered to the camera lens of a mobile device. This can provide for recording an image with an even more apparent change in the skin color. It should be noted, however, that such a filter is optional, as the processor of the mobile device can be capable of analyzing colors in the recorded image to directly recognize an increase in skin redness without the use of a filter.

The method of testing a subject for an allergy can also include warnings to the subject if a very severe allergic reaction occurs. For example, if a serious allergic reaction occurs then it can be desirable to remove the allergy skin test device immediately to avoid discomfort in the subject from the allergic reaction. In these situations, the method can include displaying instructions (e.g., on the mobile device) for the subject to remove the allergy skin test device. Such a message can also be displayed if an allergic reaction is not serious, but merely severe enough that it is clear that the allergy test has a positive result. In this situation, there is no need to keep the allergy skin test device on the skin of the subject longer than necessary. In one embodiment, the method can be performed using a mobile device. A processor of the mobile device can be used to electronically identify the allergic response severity level. A display screen of the mobile device can then be used to display an instruction to the subject to remove the allergy skin test device. The allergy skin test device can then be removed from the skin of the subject. Along these same lines, the mobile or other device can be programmed with instructions to the user on how to administer an allergy test using the allergy test device in conjunction with the mobile device, or the mobile device can comprise an application that the user can run on the mobile device that essentially guides the user through the testing procedures.

In another example, a processor of the mobile device can be used to identify a low allergic response severity level. If the skin shows a slight response, in some cases it can be useful to apply another allergy skin test device with a higher strength level to verify that the subject is allergic. When the processor of the mobile device identifies a low allergic response severity level, an instruction can be displayed on the display of the mobile device to apply an additional allergy skin test device with a higher dose of allergen to the skin. The subject can then apply the allergy skin test device with the higher dose of allergen and the test can be repeated.

Depending on the type of allergen, a "low allergic response severity level" and a "high allergic response severity level" can refer to different symptoms and types of allergic reactions. Generally, allergic response severity can be rated using a rating scale. Because different allergens can provoke different responses, each individual allergen can have its own scale. In a generic example, an allergic response severity rating scale can range from 0-10, with 10 being the most severe reaction experienced by an allergic subject, and 0 being no reaction. The scale can be divided into subranges. For example, allergic responses rated from 1-2 can be considered slight reactions or low allergic response severity level. Allergic responses rated from 3-7 can be considered a medium allergic response severity level. Allergic responses rated from 8-10 can be considered a high allergic response severity level, or generally referred to as a sever response.

In some cases, rather than a scale, the allergic response severity level can be a binary "allergic" or "not allergic" result. As an example, after an allergy test is completed the processor of the mobile device can display a message informing the subject whether or not the subject is allergic to the allergen in question.

Depending on the type of allergen, different signs of an allergic response can be used to determine the allergic response severity level. In some cases, a color change in the skin can be the primary sign of allergic response. As an example, a severe allergic response can cause a large increase in redness of skin. A slight allergic response, on the other hand, can cause a slight increase in redness. In another example, size of a red spot on the skin can be related to allergic response severity level, with a larger spot indicating a more serious response. In yet another example, an allergic response can cause a raised weal on the skin. The size of the weal can be related to the allergic response severity level.

Additionally, the method can include displaying periodic instructions to the subject, such as instructions to record an additional image of the skin. A processor of the mobile device can run a timer and display instructions at certain pre-set times. For example, an instruction can be displayed a short time after applying the allergy skin test device to record an additional image of the skin. If a moderate or severe response is detected after the short time, then an instruction can be displayed that the test result is positive and that the allergy skin test device should be removed. In some examples, the short time can be 5 minutes, 10 minutes, half an hour, or another time that is appropriate for the allergen in question. An instruction to record an additional image of the skin can also be displayed at a normal test end time. For example, the allergy test can be calibrated to end after 5 minutes, 30 minutes, 1 hour, 4 hours, 8 hours, 24 hours, 48 hours, or any other time duration appropriate for the allergen in question. At this point, the processor of the mobile device can display an instruction to record an additional image of the skin so that the processor can evaluate a final test result. Then, the processor can display an instruction prompting the user to remove the allergy skin test device from the skin.

Each time the display of the mobile device is used to display an instruction for the subject, the instruction can be accompanied by a sound, vibration, or other notification method to get the attention of the subject or user. The portability of the mobile device can make it convenient for the subject to keep the mobile device close by even when traveling away from home. Thus, the subject can receive the instructions regarding the allergy skin test device at the appropriate times no matter where the subject is located.

Instructions to record additional images can be displayed at multiple times between the beginning of the test and the end time. In one example, an integrated camera of the mobile device can be used to record at least one additional image of the skin viewed through the skin viewing portion of the allergy skin test device, and then the processor of the mobile device can display a plot of allergic response severity level over time.

Although many features of the present technology have been described as incorporating a mobile device such as a smartphone or tablet computer, any of the described embodiments can include any suitable computer system or systems. For example, the methods described herein can be performed using personal computers, laptops, servers, clients, mobile devices, and other computer systems. Images of the skin and other images described herein can be recorded using an integrated camera of a mobile device, an integrated camera of a laptop, a webcam attached to a computer system, a portable digital camera, a scanner, or other imaging device operable with or connected to a processor. Various combinations of computer systems can be used to perform the various method steps described herein. For example, some method steps can be performed using a mobile device, while others are performed using a server. Therefore, the present technology is not limited to any particular computer system or combination of computer systems.

Figure 7:
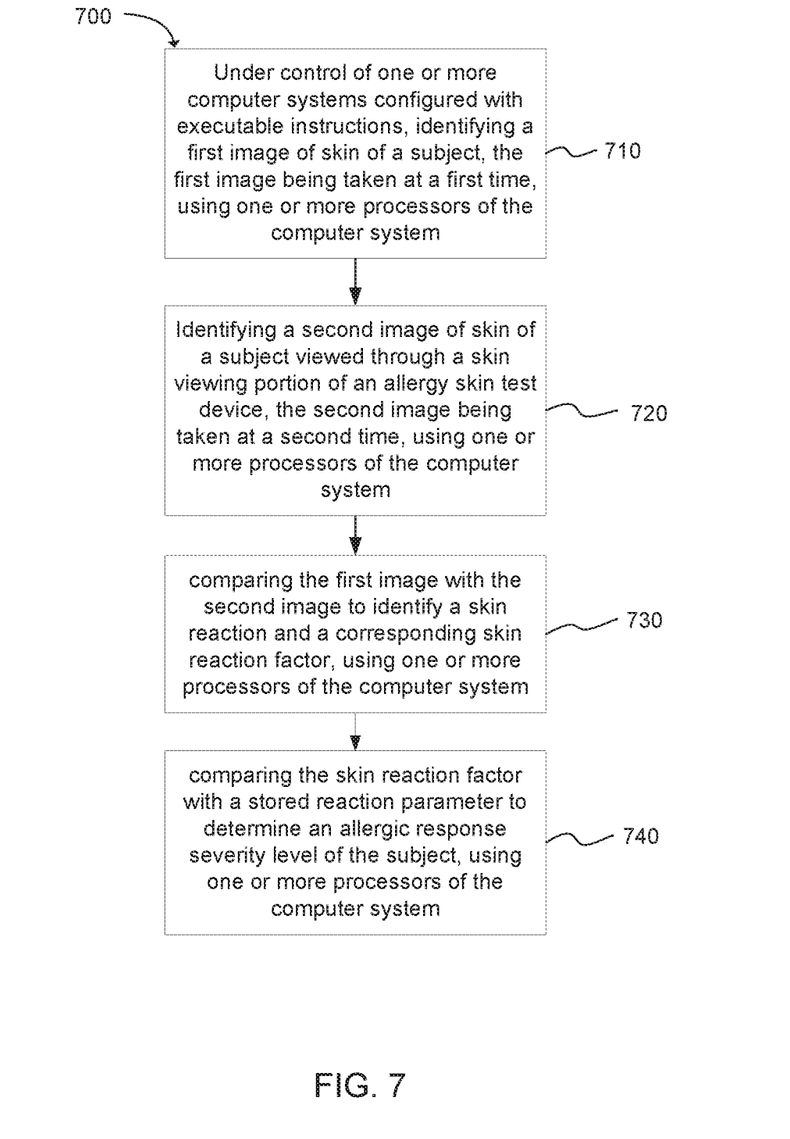
FIG. 7 is a flowchart illustrating a method of identifying an allergic response in accordance with an embodiment of the present invention.

The present technology also extends to methods of identifying allergic reactions that can be performed using computer systems. A flowchart illustrating one such method is shown in FIG. 7. A method 700 of identifying an allergic response can be performed under control of one or more computer systems configured with executable instructions. The method can include identifying a first image of skin of a subject 710. The first image can be taken at a first time. The image can be identified using one or more processors of the computer system. A second image can also be identified using one or more processors of the computer system 720. The second image can be of the skin of the subject viewed through a skin viewing portion of an allergy skin test device. The second image can be taken at a second time. The method can further include comparing the first image with the second image, using one or more processors of the computer system 730. The images can be compared to identify a skin reaction and a corresponding skin reaction factor. The skin reaction factor can be compared with a stored reaction parameter, using one or more processors of the computer system 740. By this comparison, an allergic response severity level of the subject can be determined.

The comparison of the first and second images can be performed using any process suitable for finding differences between the two images that indicate an allergic response. In some cases, an allergic response can be signified by an increase in redness of the skin in the location where the allergen is applied. In other cases, an allergic response can be signified by a red spot with the size of the spot corresponding to the severity level. In yet other cases, an allergic response can be signified by a raised weal on the skin, with the size of the weal corresponding to the severity level. The first and second images can be compared by the processor of the computer system using image processing methods to identify the signs of allergic response. In one example, an average color of pixels can be calculated for each of the first and second images and then the average colors can be compared to determine if skin redness has increased. In some cases, the average color can be calculated only from the pixels representing the skin itself, and not the surrounding allergy skin test device or other parts of the images. This can be accomplished, for example, by using image recognition to locate identifying marks, symbols, or colors on the allergy skin test device, and then identifying the pixels representing the skin of the subject as viewed through the skin viewing portion of the allergy skin test device. In other examples, the size of a spot or weal on the skin can be determined from the image by using edge recognition. Edges of the spot or weal can be found, and then the diameter or area of the spot or weal can be calculated. In one example, the processor can find the edges of the skin viewing portion of the allergy skin test device and calculate the actual size of the spot or weal by comparing its apparent size in the image to the known size of the skin viewing portion of the allergy skin test device. A wide variety of image processing methods and algorithms can be used, and the present technology is not limited to the examples described herein. Rather, any image processing method suitable for finding signs of allergic response can be used.

Figure 8:
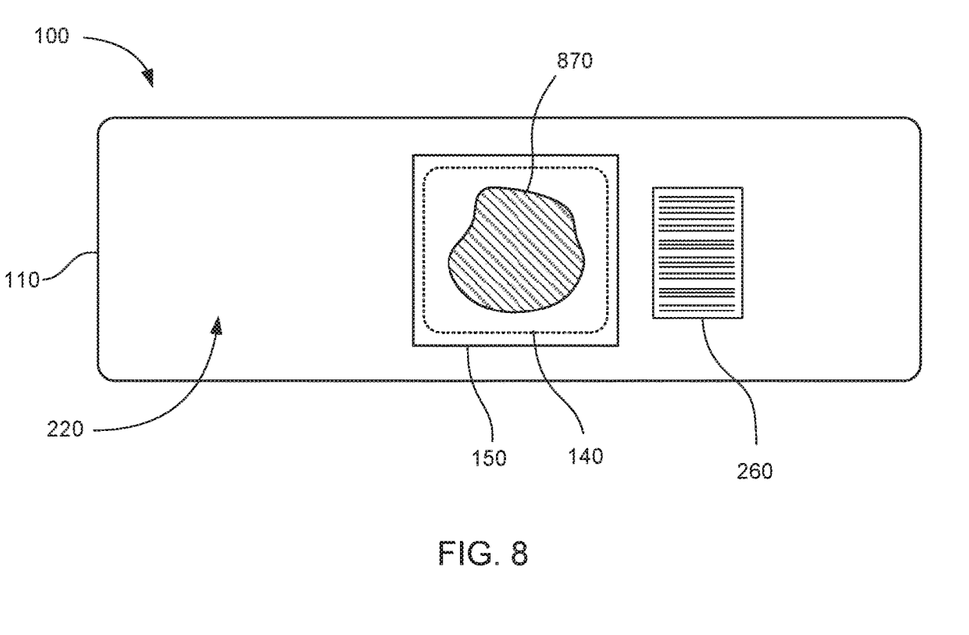
FIG. 8 is a top view of an allergy skin test device as applied to skin of a subject after an allergic response has occurred, in accordance with an embodiment of the present invention.

As an example, FIG. 8 shows an allergy skin test device 100 as applied to the skin of a subject after an allergic response has occurred. The allergic response causes a reddened spot 870 to form. The spot is shaded in the figure to represent a change in color from the original color of the skin. An image of the skin after this response has occurred can be compared with an image of the skin before the response occurred. As described above, a variety of methods can be used to electronically compare the images to identify a skin reaction. The diameter or area of the reddened spot can be calculated by comparing the apparent size of the reddened spot with the apparent size of the skin viewing portion 150. Alternately, the average pixel color inside the entire skin viewing portion can be compared with the average pixel color before the allergic response. Edge recognition can also be used to isolate the reddened spot and compare the average color of the reddened spot with the average color of the skin before the allergic response.

The processor can identify a skin reaction by comparing the first and second images. The skin reaction refers to the physical change in the skin of the patient that signifies an allergic response. The processor can also identify a corresponding skin reaction factor. The skin reaction factor can be any numerical value used by the processor to represent the allergic reaction. For example, the skin reaction factor can be a difference between average pixel colors, a diameter of a weal, or other factor that describes the extent of the allergic reaction. Because different types of allergens can produce different types of allergic responses, the skin reaction factor can be different for each type of allergen. In some cases, multiple skin reaction factors can be used. For example, a first skin reactions factor can be a difference in average pixel colors, representing an increased redness of the skin. A second skin reaction factor can be a diameter of a red spot on the skin. Both of these reaction factors may be used together to determine an allergic response severity level.

An allergic response severity level can be determined by comparing the skin reaction factor with a stored reaction parameter. The stored reaction parameter can be a numerical value that can be used in conjunction with the skin reaction factor to identify or calculate the allergic response severity level of the subject. Stored reaction parameters can be determined ahead of time through study of the allergens and collection of data. As an example, allergens can be applied to known allergic individuals, and the type of allergic response experienced by the individuals can be recorded. By collecting data from a large number of individuals, a range of allergic response severity levels from slight responses to severe responses can be correlated with different skin reactions. These different skin reactions can be stored as stored reaction factors, for example in a database.

A variety of algorithms can be used to compare the skin reaction factor measured during an allergy test with the stored reaction factors for the particular allergen in question in order to determine the allergic reaction severity level of the subject being tested. Therefore, present technology is not limited to the specific examples described herein. However, as one example, the stored reaction parameter can be a threshold value for a particular allergic response severity level. If the skin reaction factor is an average color difference, then the stored reaction parameter can be a threshold value for an allergic response severity level of 1. The processor of the computer system can compare the skin reaction factor with the stored reaction parameter, and if the skin reaction factor is higher, then the subject has an allergic response severity level of at least 1. The processor can then compare the skin reaction factor with the next stored reaction parameter to determine if the subjects allergic response severity level is at least 2, and so on until the allergic response severity level is determined.

In one example, the stored reaction parameter and the skin reaction factor can be percentages of reflected light that has a red color. An initial percentage of red reflected light can be measured at the beginning of the allergy test. A second percentage of red reflected light can be measured after an elapsed time. The difference between the percentages can be compared to stored values of percentage or red reflected light that correspond to various severity levels. For example, a range between a minimum and maximum percentage of red reflected light can be divided into 10 divisions, and the severity level can be assigned based on which division matches the percentage of red reflected light from the subject's skin.

In another example, the stored reaction parameter can include a mathematical formula or function that can receive the skin reaction factor as input and then output the allergic response severity level. Such a function can be developed by studying test data from a large number of individuals, and then using curve-fitting or other methods to fit a function to the data.

In yet another example, the skin reaction factor and stored reaction parameter can include measurements based on increased heat of the skin caused by an allergic response. Viewing the skin of the subject using a near-infrared or infrared camera can show increased heat from an allergic response. Some commercially available mobile devices already include cameras that are able to sense near-infrared radiation. In another example, a thermally sensitive ink can be printed on the test device that changes color with heat from inflamed skin. The change in color of the ink can also serve as a skin reaction factor and a stored reaction parameter for identifying allergic responses. In some cases, such a thermally sensitive ink can include a thermochromic material such as thermochromatic liquid crystals or leuco dyes. The change in color of the thermochromics material can be detected electronically and can also serve as a visible indicator to the subject that a reaction is occurring.

In further examples of methods of identifying an allergic response, an instruction for the subject can be displayed on an electronic display in communication with the computer system. The instruction can be any of the instructions described herein, such as instructions to record additional images of the subject's skin or to remove the allergy skin test device. In further examples, the instruction can change based on the allergic response severity level. For example, if an allergic response severity level is calculated a short time after beginning the test (such as 5 minutes, 10 minutes, or 30 minutes) and the allergic response severity level is low (e.g., 1 or 2 on a scale of 1-10), then the instruction can prompt the subject to leave the allergy skin test device on longer to wait and see if the allergic response worsens over time. The instruction can also include a message explaining that a slight allergic reaction was detected, but that the test should continue for a longer time to verify the reaction. The computer system can also be programmed to modify the time schedule for recording additional images in this situation. For example, the time at which another image should be recorded to recalculate the allergic response severity level can be moved forward from the original schedule. Then, at the new time for recording an additional image, the computer system can display another instruction for the subject to record an additional image.

In another example, a severe allergic reaction after a short period of time can cause the computer system to display an instruction for the subject to remove the allergy skin test device immediately before any more adverse reaction occurs.

At the end of a test, an instruction can be displayed prompting the subject how to proceed. For example, if the allergy test is negative then an instruction can be displayed informing the subject that the subject is not allergic to the allergen in question. If the subject is allergic, the instruction can inform the subject of the allergy and the allergic response severity level. The test device can be packaged with multiple test devices of different strengths. In some cases, the instruction can prompt the user to apply another test device with stronger or weaker allergen strength. The instruction can also prompt the subject to seek advice or a prescription from a healthcare professional if needed. In some cases, the instruction can provide information to help the subject avoid allergic reactions, such as listing possible foods to avoid eating that could contain the allergen.

In another embodiment, the method can include displaying, on an electronic display in communication with the computer system, a prompt for the subject to record the first image using a digital camera in communication with the computer system, using one or more processors of the computer system. Then, the processor can delay for a sufficient time to enable an allergic response to occur. After the time has passed, another prompt can be displayed on the electronic display prompting the subject to record a second image using the digital camera.

In yet another embodiment, the method can include activating a light source in communication with the computer system to illuminate the skin during the recording of the first and second images. The light source can provide the same light intensity for each image, or vary the light intensity depending on the distance from the light source to the skin of the subject so that the skin receives consistent illumination. As described above, the light source can also be configured to emit a wavelength of light selected to increase visibility of the allergic response.

In a further embodiment, at least one of the first image and second image can show an identification code printed on the allergy skin test device. The processor of the computer system can identify the allergen based on the identification code. The processor can also identify other information about the allergy skin test device, such as a strength level, an allergen dosage, presence of lack of micro spicules, and so on. This information can then be used by the processor to identify the correct skin reaction factors and stored reaction parameters to be used in calculating the allergic response severity level.

PROPHETIC EXAMPLES

Example 1

An allergy skin test device is prepared by forming a flexible support strip with a transparent window at the center. Ground peanuts mixed with adhesive are applied to the bottom surface of the transparent window. Adhesive without the peanut allergen is applied to the remaining bottom surface of the support strip. The allergy skin test device has a machine-readable bar code printed on the top surface near the transparent window.

Example 2

The allergy skin test device of Example 1 is applied to the skin of a subject. The subject uses a smartphone running an application programmed to work together with the allergy skin test device. The smartphone application prompts the subject to take a photograph of the transparent window immediately after applying the allergy skin test device to the skin. The subject takes the photograph using the integrated digital camera of the smartphone, and in some cases a light filtering function can be provided and utilized as needed. This photograph is stored in the smartphone's memory. The smartphone application reads the bar code on the allergy skin test device from the photograph, and identifies the allergy skin test device as a peanut allergy test. The smartphone application downloads and/or accesses pre-stored data about the peanut allergy test, including time periods between photographs, skin reaction factors, stored reaction parameters, and instructions for the subject.

After a period of 30 minutes, the smartphone application prompts the subject to take another photograph. The subject takes the second photograph using the integrated camera of the smartphone. The smartphone application compares the first photograph with the second photograph. The smartphone application identifies the skin reaction factor for the peanut allergy test to be change in red value in the average pixel color of the skin exposed to the allergen. Using edge recognition, the smartphone application isolates the area inside the transparent window and then compares the average pixel colors of the first photograph and the second photograph. Using the RGB color scale of 0-255 for red, green, and blue, the smartphone application finds that the average red value increased by 2 points from the first photograph to the second photograph. The smartphone application compares the increase in red value with the stored reaction parameter for a slight (level 1) reaction. The stored reaction parameter for a level 1 reaction for the peanut allergy test is a 5 point increase in red value. Because the actual increase in red value is below this threshold, the smartphone application identifies no sign of reaction and displays an instruction for the subject to continue the test.

After 24 hours, the smartphone application prompts the subject to take another photograph. The smartphone application compares this third photograph with the first photograph in the same way described above. The difference in red value is calculated to be 15 points. The smartphone application determines that this value is between the stored reaction parameter for a level 3 reaction (12 points on the red scale) and the stored reaction parameter for a level 4 reaction (16 points on the red scale). The smartphone displays and instruction to the subject informing the subject that the subject has a level 3, or moderate, peanut allergy.

It is to be understood that the embodiments of the technology disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to "one embodiment" or "an embodiment" means that a particular feature, structure, or characteristic described in connection with the embodiment is included in at least one embodiment of the present technology. Thus, appearances of the phrases "in one embodiment" or "in an embodiment" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present technology.

Furthermore, the described features, structures, or characteristics may be combined in any suitable manner in one or more embodiments. In the description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the technology.

While the foregoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the present technology. Accordingly, it is not intended that the present technology be limited, except as by the claims set forth below.

What is claimed is:
1. A method of testing a subject for an allergy, comprising:
 a) applying an allergy skin test device to an area of skin of the subject, such that an allergen of an allergen portion of the allergy skin test device is caused to come into contact with the skin;
 b) recording a first image of the skin of the subject prior to an allergic response;
 c) waiting a sufficient time to enable an allergic response to occur;
 d) recording a second image of the skin of the subject viewed through a skin viewing portion of the allergy skin test device;
 e) electronically comparing the first image with the second image to identify a skin reaction and a corresponding skin reaction factor; and
 f) electronically comparing the skin reaction factor with a stored reaction parameter to determine an allergic response severity level of the subject,
 wherein the allergy skin test device comprises:
  a support strip having a top face and a bottom face,
  an allergen applied to an area of the bottom face forming an allergen portion,
  a skin viewing portion formed within the support strip and located proximate or at the allergen portion, and
  an adhesive applied to an area of the bottom face forming an adhesion portion,
  wherein the allergy skin test device facilitates viewing of a portion of the skin beneath the allergy skin test device through the skin viewing portion.
2. The method of claim 1, wherein the allergy skin test device comprises an identification code printed on the top face of the support strip, wherein the identification code identifies a characteristic of the allergen.

3. The allergy skin test device of claim 2, wherein the characteristic is selected from the group consisting of type of allergen, class of allergen, expiration date, date of manufacture, allergen strength, and combinations thereof.

4. The method of claim 2, further comprising using an integrated camera of a mobile device to scan the identification code.

5. The method of claim 1, wherein the first image is of the skin of the subject viewed through the skin viewing portion of the allergy skin test device.

6. The method of claim 1, wherein the allergy skin test device comprises a thermochromic material configured to change color with changing temperature of the skin of the subject, and wherein the method further comprises identifying a change in color of the thermochromics material.

7. The method of claim 1, wherein recording the first image and recording the second image are performed using an integrated camera of a mobile device.

8. The method of claim 7, further comprising using an integrated light of the mobile device to illuminate the skin of the subject when recording the first image and the second image.

9. The method of claim 8, wherein the integrated light is configured to emit a wavelength of light selected to improve detectability of the skin reaction.

10. The method of claim 7, further comprising:
using a processor of the mobile device, identifying the allergic response severity level;
displaying an instruction on a display of the mobile device to remove the allergy skin test device; and
removing the allergy skin test device from the skin of the subject.

11. The method of claim 7, further comprising:
using a processor of the mobile device, identifying a low allergic response severity level and displaying an instruction on a display of the mobile device to apply an additional allergy skin test device to the skin; and
applying additional allergy skin test device to the skin, wherein the additional allergy skin test device has a higher dose of the allergen compared to the first allergy skin test device.

12. The method of claim 7, further comprising using the integrated camera of the mobile device to record at least one additional image of the skin of the subject viewed through the skin viewing portion of the allergy skin test device as applied to the subject, and using the processor of the mobile device to display a plot of the allergic response severity level over time.

13. A method for identifying an allergic reaction, the method comprising
under control of one or more computer systems configured with executable instructions:
identifying a first image of skin of a subject, the first image being taken at a first time, using one or more processors of the computer system;
identifying a second image of skin of a subject viewed through a skin viewing portion of an allergy skin test device, the second image being taken at a second time, using one or more processors of the computer system;
comparing the first image with the second image to identify a skin reaction and a corresponding skin reaction factor, using one or more processors of the computer system; and comparing the skin reaction factor with a stored reaction parameter to determine an allergic response severity level of the subject, using one or more processors of the computer system,
wherein the allergy skin test device comprises:
a support strip having a top face and a bottom face,
an allergen applied to an area of the bottom face forming an allergen portion,
a skin viewing portion formed within the support strip and located proximate or at the allergen portion, and
an adhesive applied to an area of the bottom face forming an adhesion portion,
wherein the allergy skin test device facilitates viewing of a portion of the skin beneath the allergy skin test device through the skin viewing portion.

14. The method of claim 13, further comprising displaying, on an electronic display in communication with the computer system, an instruction for the subject based on the allergic response severity level, using one or more processors of the computer system.

15. The method of claim 13, further comprising:
displaying, on an electronic display in communication with the computer system, a prompt for the subject to record the first image using a digital camera in communication with the computer system, using one or more processors of the computer systems;
delaying a sufficient time to enable an allergic response to occur, using one or more processors of the computer system; and
displaying, on the electronic display in communication with the computer system, a prompt for the subject to record the second image using the digital camera in communication with the computer system, using one or more processors of the computer system.

16. The method of claim 15, further comprising activating a light source in communication with the computer system to illuminate the skin during recording of the first and second images, using one or more processors of the computer system.

17. The method of claim 15, further comprising alerting the subject of the prompt by producing vibrations from a vibration device in communication with the computer system or an audible sound in communication with the computer system, using one or more processors of the computer system.

18. The method of claim 15, further comprising delaying an additional time using one or more processors of the computer system and displaying an additional prompt for the subject to record an additional image using the digital camera in communication with the computer system, using one or more processors of the computer system.

19. The method of claim 13, wherein comparing the first image with the second image comprises using one or more processors of the computer system.

20. The method of claim 13, wherein at least one of the first image and second image shows an identification code printed on the allergy skin test device, the method further comprising identifying the allergen based on the identification code, using one or more processors of the computer system.

21. The method of claim 13, wherein the first image and second image are taken using an infrared or near-infrared camera to detect emitted heat from the skin of the subject, using one or more processors of the computer system.

22. The method of claim 13, wherein the allergy skin test device comprises a thermochromic material configured to change color with changing temperature of the skin of the subject, and wherein the method further comprises identifying a change in color of the thermochromic material using one or more processors of the computer system.

\* \* \* \* \*